(12) United States Patent
Kartoun et al.

(10) Patent No.: US 11,742,081 B2
(45) Date of Patent: Aug. 29, 2023

(54) DATA MODEL PROCESSING IN MACHINE LEARNING EMPLOYING FEATURE SELECTION USING SUB-POPULATION ANALYSIS

(71) Applicants: International Business Machines Corporation, Armonk, NY (US); Massachusetts Institute of Technology, Cambridge, MA (US)

(72) Inventors: Uri Kartoun, Cambridge, MA (US); Kristen Severson, Somerville, MA (US); Kenney Ng, Arlington, MA (US); Paul D. Myers, Bloomfield Hills, MI (US); Wangzhi Dai, Cambridge, MA (US); Collin M. Stultz, Newton, MA (US)

(73) Assignees: International Business Machines Corporation, Armonk, NY (US); Massachusetts Institute of Technology, Cambridge, MA (US)

( * ) Notice: Subject to any disclaimer, the term of this patent is extended or adjusted under 35 U.S.C. 154(b) by 634 days.

(21) Appl. No.: 16/863,452

(22) Filed: Apr. 30, 2020

(65) Prior Publication Data
US 2021/0343421 A1    Nov. 4, 2021

(51) Int. Cl.
*G16H 40/67* (2018.01)
*G16H 50/50* (2018.01)
(Continued)

(52) U.S. Cl.
CPC ............ *G16H 40/67* (2018.01); *G06F 17/18* (2013.01); *G06F 18/23* (2023.01); *G16H 50/50* (2018.01); *G16H 50/70* (2018.01)

(58) Field of Classification Search
CPC ........ G16H 50/50; G16H 50/70; G16H 40/67; G16H 50/20; G06F 17/18; G06K 9/6218
See application file for complete search history.

(56) References Cited

U.S. PATENT DOCUMENTS 7,415,445 B2    8/2008    Forman
7,542,959 B2    6/2009    Barnhill et al.
(Continued)

OTHER PUBLICATIONS

P. Myers, "Choosing Clinical Variables for Risk Stratification Post-Acute Coronary Syndrome" Scientific Reports, vol. 9, article No. 14631, 2019, 9 pages.
(Continued)

*Primary Examiner* — Eliza A Lam
(74) *Attorney, Agent, or Firm* — Edell, Shapiro & Finnan, LLC

(57) ABSTRACT

A computer system selects features of a dataset for predictive modeling. A first set of features that are relevant to outcome are selected from a dataset comprising a plurality of cases and controls. A subset of cases and controls having similar values for the first set of features is identified. The subset is analyzed to select a set of additional features relevant to outcome. A first and second predictive model are evaluated to determine that the second predictive model more accurately predicts outcome, wherein the first predictive model is based on the first set of features and the second predictive model is based on the first set of features and the additional features. The second predictive model is utilized to predict outcomes. Embodiments of the present invention further include a method and program product for selecting features of a dataset for predictive modeling in substantially the same manner described above.

20 Claims, 7 Drawing Sheets

(51) Int. Cl.
  G06F 17/18 (2006.01)
  G16H 50/70 (2018.01)
  G06F 18/23 (2023.01)

(56) References Cited

U.S. PATENT DOCUMENTS

| | | | |
|---|---|---|---|
| 7,624,074 | B2 | 11/2009 | Weston et al. |
| 8,301,638 | B2 | 10/2012 | Xu et al. |
| 9,189,750 | B1 | 11/2015 | Narsky |
| 2005/0049913 | A1 | 3/2005 | Huddleston et al. |
| 2005/0131847 | A1 | 6/2005 | Weston et al. |
| 2005/0216426 | A1 | 9/2005 | Weston et al. |
| 2008/0004865 | A1 | 1/2008 | Weng et al. |
| 2008/0033899 | A1 | 2/2008 | Barnhill et al. |
| 2010/0193309 | A1 | 8/2010 | Gruber et al. |
| 2011/0078099 | A1 | 3/2011 | Weston et al. |
| 2011/0307437 | A1 | 12/2011 | Aliferis et al. |
| 2012/0041772 | A1* | 2/2012 | Ebadollahi ............ G16H 50/70 705/2 |
| 2012/0310785 | A1* | 12/2012 | Poulin ................ G06Q 10/0637 707/769 |
| 2014/0279754 | A1* | 9/2014 | Barsoum ................ G06N 7/005 706/12 |
| 2016/0110656 | A1 | 4/2016 | Yamada et al. |
| 2019/0108915 | A1 | 4/2019 | Spurlock, III |
| 2019/0311805 | A1 | 10/2019 | Linguraru et al. |
| 2019/0370684 | A1 | 12/2019 | Gunes et al. |
| 2021/0342735 | A1 | 11/2021 | Kartoun et al. |

OTHER PUBLICATIONS

R. Guo et al., "A Survey of Learning Causality with Data: Problems and Methods." (Submitted on Sep. 25, 2018 (v1), last revised Apr. 19, 2019 (this version, v3)), 36 pages.
J. Ross et al. "Can machine learning complement traditional medical device surveillance? A case study of dual-chamber implantable cardioverter-defibrillators." Medical Devices (Auckland, N.Z.) vol. 10, pp. 165-188. Aug. 16, 2017, 28 pages.
W. Rivera, "A Priori Synthetic Sampling for Increasing Classification Sensitivity in Imbalanced Data Sets." Ph.D. dissertation, College of Engineering and Computer Science at the University of Central Florida Orlando, Florida, 2016, 245 pages.
M. Ammad-Ud-Din et al., "Systematic identification of feature combinations for predicting drug response with Bayesian multi-view multi-task linear regression." Bioinformatics, 33, i359-i368, 2017, 10 pages.
A. Chatterjee, et al., "Bootstrapping Lasso Estimators", Journal of the American Statistical Association, Jun. 2011, vol. 106, No. 494, Theory and Methods, 18 pages.
H. Zou, "The Adaptive Lasso and Its Oracle Properties", Journal of the American Statistical Association, Dec. 2006, vol. 101, No. 476, Theory and Methods, 12 pages.
P. Myers, et al., "Machine Learning Improves Risk Stratification After Acute Coronary Syndrome", Scientific Reports, vol. 7, article No. 12692, 2017, 12 pages.
M. Paul, "Feature Selection as Causal Inference: Experiments with Text Classification", Proc. 21st Conference on Computational Natural Language Learning (CoNLL 2017), pp. 163-172, Vancouver, Canada, Aug. 3-Aug. 4, 2017, 10 pages.
K. Imai, et al., "Estimating Treatment Effect Heterogeneity in Randomized Program Evaluation", The Annals of Applied Statistics, vol. 7, No. 1, pp. 443-470, 2013, 28 pages.
J. Sekhon, "Package "Matching" (Multivariate and Propensity Score Matching with Balance Optimization)," May 2019, Version 4.9-6, 36 pages.
J. Tang, et al, "Feature Selection for Classification: A Review", https://www.cc.gatech.edu/~hic/CS7616/Papers/Tang-et-al-2014. pdf. Data classification: Algorithms and applications (2014): 37, 33 pages.
Wikipedia, "Feature selection", https://en.wikipedia.org/wiki/Feature_selection, downloaded from the internet on Apr. 30, 2020, 15 pages.
Wikipedia, "MELD-Plus", https://en.wikipedia.org/wiki/MELD-Plus, downloaded from the internet on Apr. 30, 2020, 4 pages.
K. A. A. Fox, et al., "Management of acute coronary syndromes. Variations in practice and outcome", Findings from the Global Registry of Acute Coronary Events (GRACE), European Heart Journal (2002) 23, 1177-1189, https://www.ncbi.nlm.nih.gov/pubmed/12127920, 13 pages.
R. Guo, et al., "A Survey of Learning Causality with Data: Problems and Methods", arXiv:1809.09337v3 [cs.AI], Apr. 19, 2019, 36 pages.
J. Ross, et al., "Can machine learning complement traditional medical device surveillance? A case study of dual-chamber implantable cardioverter-defibrillators", Medical Devices: Evidence and Research 2017:10 165-188, 24 pages.
W. Rivera, "a priori synthetic sampling for increasing classification sensitivity in imbalanced data sets", (2016) Electronic Theses and Dissertations, 2004-2019, 4895, 245 pages.
M. Ammad-Ud-Din, et al., "Systematic identification of feature combinations for predicting drug response with Bayesian multi-view multi-task linear regression", Bioinformatics, 33, 2017, i359-i368, 10 pages.
H. Zou, "The Adaptive Lasso and it's Oracle Properties", Journal of the American Statistical Association, 101:476; 1418-1429, DOI: 10.1198/016214506000000735, (2006), 13 pages.
List of IBM Patents or Patent Applications Treated as Related, filed May 20, 2020.

* cited by examiner

| N_CASES | N_CONTROLS | CONTROLS_PER_CASE | CALIPER | AUC | AUC_ABS_DIFF_0.5 |
|---|---|---|---|---|---|
| 3065 | 3065 | 1 | 2.05 | 0.499921575 | 7.84E-05 |
| 3066 | 3066 | 1 | 4.65 | 0.499901586 | 9.84E-05 |
| 3066 | 3066 | 1 | 3.7 | 0.499898934 | 0.000101660 |
| 3066 | 3066 | 1 | 3.1 | 0.500167169 | 0.000167169 |
| 3065 | 3065 | 1 | 2.55 | 0.500224464 | 0.000224464 |
| 2479 | 7437 | 3 | 0.1 | 0.499626723 | 0.000373277 |
| 3065 | 3065 | 1 | 2.45 | 0.499959474 | 0.000405260 |
| 2778 | 5556 | 2 | 0.55 | 0.499574345 | 0.000425655 |
| 3066 | 3066 | 1 | 3.2 | 0.500453553 | 0.000453553 |
| 2988 | 2988 | 1 | 0.6 | 0.500529162 | 0.000529162 |
| 3066 | 3066 | 1 | 3.15 | 0.500577711 | 0.000577711 |
| 6034 | 3034 | 1 | 1.05 | 0.499365913 | 0.000634087 |
| 3042 | 3042 | 1 | 1.2 | 0.500635084 | 0.000635084 |
| 3066 | 3066 | 1 | 3.85 | 0.499339276 | 0.000660724 |
| 3012 | 3012 | 1 | 0.8 | 0.499931259 | 0.000387410 |
| 2541 | 7623 | 3 | 0.4 | 0.500718672 | 0.000718672 |
| 3066 | 3066 | 1 | 4.9 | 0.499168047 | 0.000831953 |

FIG.4

DATA MODEL PROCESSING IN MACHINE LEARNING EMPLOYING FEATURE SELECTION USING SUB-POPULATION ANALYSIS

BACKGROUND

1. Technical Field

Present invention embodiments relate to machine learning, and more specifically, to improving computerized processing of data models used in machine learning by enhancing feature selection using sub-population analysis.

2. Discussion of the Related Art

In the field of machine learning, feature selection, also known as variable selection or attribute selection, refers to the process of selecting relevant data features for use in model construction. While a dataset can contain any number of features, feature selection techniques identify a subset of features that are the most useful for a data model. In particular, features that are irrelevant or redundant can typically be omitted from consideration without negatively impacting the performance of a corresponding data model. However, feature selection techniques can fail to identify some features that are nevertheless informative.

SUMMARY

According to one embodiment of the present invention, a computer system selects features of a dataset for predictive modeling. A first set of features that are relevant to outcome are selected from a dataset comprising a plurality of cases and controls. A subset of cases and controls having similar values for the first set of features is identified. The subset of cases and controls is analyzed to select a second set of additional features that are relevant to outcome. Performance of a first predictive model is evaluated against performance of a second predictive model to determine that the second predictive model more accurately predicts outcome, wherein the first predictive model is based on the first set of features and the second predictive model is based on the first set of features and the second set of additional features. The second predictive model is utilized to predict outcomes. Embodiments of the present invention further include a method and program product for selecting features of a dataset for predictive modeling in substantially the same manner described above. Thus, present invention embodiments increase the accuracy of computerized predictive models, and additionally, increase processing efficiency by reducing the likelihood that processing resources are misallocated to the forecasting of outcomes that are ultimately erroneous.

Various other embodiments of the present invention will now be discussed. In some embodiments, the subset of cases and controls is identified by identifying a plurality of case-control matchings by applying propensity score matching with different combinations of caliper values and case-control ratio values to the dataset to match cases with controls, comparing, for each case-control matching, values of the cases to values of the controls to determine a similarity value, wherein the compared values comprise values for the first set of features, and selecting a case-control matching based on a ranking of similarity values of the plurality of case-control matchings. Thus, cases are matched with controls that are similar, thereby identifying a subset of cases and controls that is conducive for identifying other features that can explain the difference in outcome. In some embodiments, the similarity value for each case-control matching is determined by dividing cases and controls of the case-control matching into a training set and a testing set, training a predictive model using the training set, testing the predictive model using the testing set to identify true positives and false positives, and calculating the similarity value by determining an area under a receiver operating characteristic curve, wherein the receiver operating characteristic curve is based on the identified true positives and false positives. Thus, a normalized value can be computed to quantify the similarity of a group of cases to a group of controls, facilitating comparisons of the two groups. In some embodiments, evaluating performance of the first predictive model against the second predictive model comprises testing each of the first predictive model and the second predictive model using a same model testing set to identify true positives and false positives, and comparing a first area under a first receiver operating curve to a second area under a second receiver operating curve, wherein the first receiver operating curve is based on identified true and false positives of the first predictive model and wherein the second receiver operating curve is based on identified true and false positives of the second predictive model. Thus, present invention embodiments verify that a generated predictive model is superior in predictive accuracy. In some embodiments, the second set of additional features is identified based on a statistical significance of each feature satisfying a threshold significance value to predict the outcome. Thus, features that were not selected initially but may be most relevant to determining outcome can be identified. In some embodiments, the statistical significance is determined using one or more of: a chi square test, a t-test, and a non-parametric test. By applying different types of statistical tests, statistical significance can be determined for values that are categorical, normally distributed, and/or not normally distributed. In some embodiments, the dataset comprises clinical data and wherein the outcome comprises a medical outcome. Thus, a predictive model can be developed and applied to other clinical data to predict outcomes more accurately.

BRIEF DESCRIPTION OF THE DRAWINGS

Generally, like reference numerals in the various figures are utilized to designate like components.

FIG. 4 is a table depicting attributes of subpopulations in accordance with an embodiment of the present invention;

DETAILED DESCRIPTION

Figure 1:
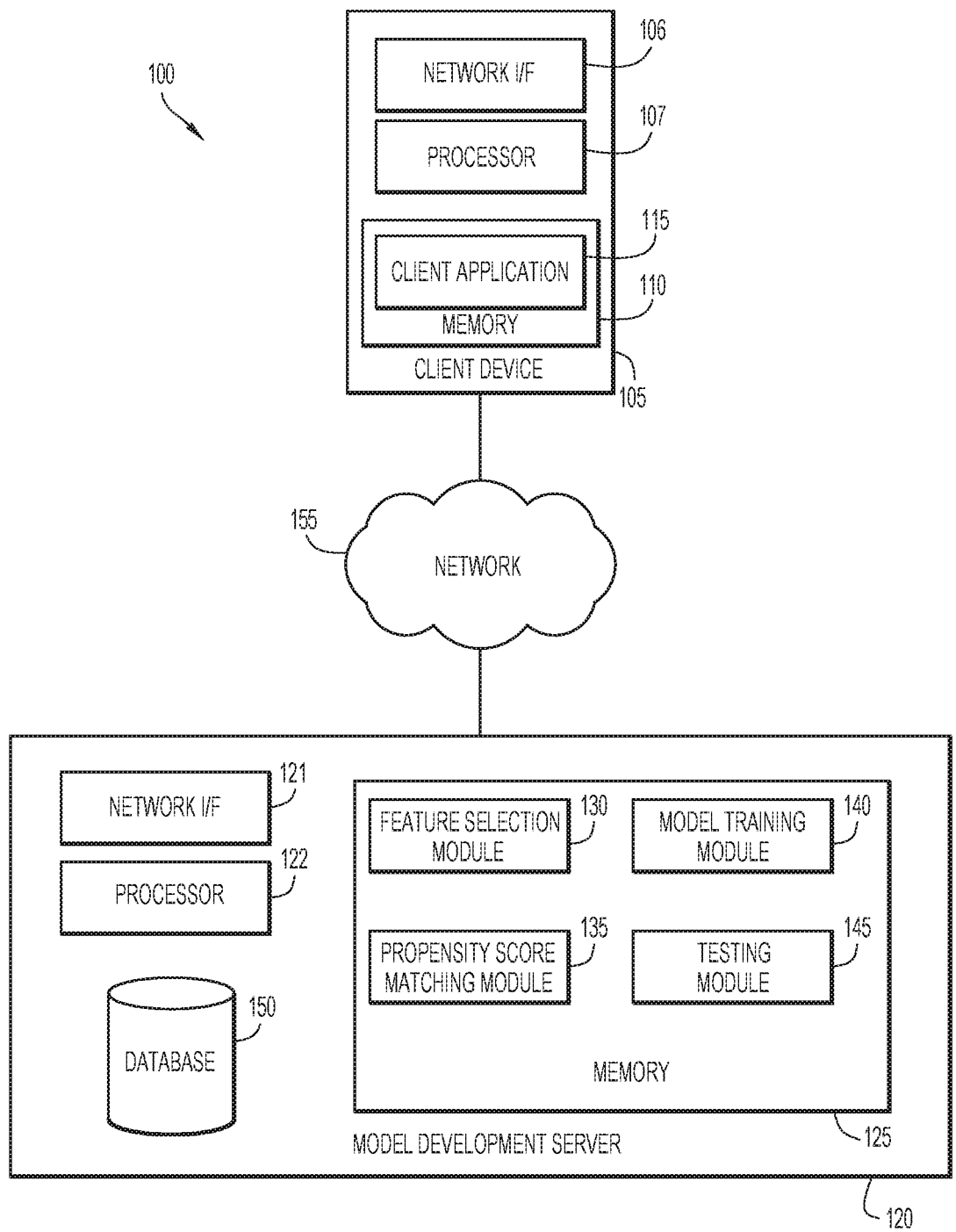
FIG. 1 is a block diagram depicting a computing environment for model development in accordance with an embodiment of the present invention.

Present invention embodiments relate to machine learning, and more specifically, to improving the computerized processing of data models used in machine learning by enhancing feature selection using sub-population analysis. A predictive model refers to a data model that processes input data to forecast a selected outcome. For example, a predictive model may process clinical data of a patient to determine the most likely outcome of the patient (e.g., recovery from a disease). In order to develop such a model, machine learning techniques may be applied to train the model using a training sample of example clinical data that includes both types of outcome (e.g., recovered vs. not recovered from a disease). A feature selection technique may identify certain data features in particular that are most useful as indicators of, or proxies for, the outcome of interest; the selected features are then used to develop a predictive model. It should be noted that the term "feature" could also be referred as "variable," "covariate", or "attribute".

Often, the feature selection process can fail to identify some features that are nevertheless informative of an outcome, resulting in a training set that excludes useful data to the detriment of any models trained with the training set. For example, when a useful feature is not selected, a resulting trained model may have a higher rate of false positives as compared to a model whose training set includes the feature. Present invention embodiments improve the performance of trained data models by enhancing the feature selection process to produce superior prediction performance. In particular, a dataset is analyzed to select features, and a subpopulation of the dataset is identified that includes both cases (i.e., records having the selected outcome) and controls (i.e., records not having the selected outcome) whose values are similar in terms of the previously-selected features. Feature selection is again performed on the subpopulation in order to identify additional relevant features.

Thus, present invention embodiments analyze a subpopulation of cases and controls that can appear quite similar to each other in some respects, despite having different outcomes. Additional features may then be identified that are potentially useful to distinguish the difference in outcomes of the cases and controls. These additional features can be used to train a new data model whose performance can be compared to a data model trained only on the initially-identified features in order to verify that the additional features are indeed useful for more accurately predicting the outcome of interest.

By increasing the performance of predictive models, present invention embodiments increase the accuracy of outcome forecasting. Any data-related application will benefit from this increased performance, including such use cases as health care, user analytics, and the like. Moreover, present invention embodiments increase processing efficiency by reducing the likelihood that processing resources are misallocated to the forecasting of outcomes that are ultimately erroneous.

Various other embodiments of the present invention will now be discussed. In some embodiments, the subset of cases and controls is identified by identifying a plurality of case-control matchings by applying propensity score matching with different combinations of caliper values and case-control ratio values to the dataset to match cases with controls, comparing, for each case-control matching, values of the cases to values of the controls to determine a similarity value, wherein the compared values comprise values for the first set of features, and selecting a case-control matching based on a ranking of similarity values of the plurality of case-control matchings. Thus, cases are matched with controls that are similar, thereby identifying a subset of cases and controls that is conducive for identifying other features that can explain the difference in outcome. In some embodiments, the similarity value for each case-control matching is determined by dividing cases and controls of the case-control matching into a training set and a testing set, training a predictive model using the training set, testing the predictive model using the testing set to identify true positives and false positives, and calculating the similarity value by determining an area under a receiver operating characteristic curve, wherein the receiver operating characteristic curve is based on the identified true positives and false positives. Thus, a normalized value can be computed to quantify the similarity of a group of cases to a group of controls, facilitating comparisons of the two groups. In some embodiments, evaluating performance of the first predictive model against the second predictive model comprises testing each of the first predictive model and the second predictive model using a same model testing set to identify true positives and false positives, and comparing a first area under a first receiver operating curve to a second area under a second receiver operating curve, wherein the first receiver operating curve is based on identified true and false positives of the first predictive model and wherein the second receiver operating curve is based on identified true and false positives of the second predictive model. Thus, embodiments of the present invention verify that a generated predictive model is superior in predictive accuracy. In some embodiments, the second set of additional features is identified based on a statistical significance of each feature satisfying a threshold significance value to predict the outcome. Thus, features that were not selected initially but may be most relevant to determining outcome can be identified. In some embodiments, the statistical significance is determined using one or more of: a chi square test, a t-test, and a non-parametric test. By applying different types of statistical tests, statistical significance can be determined for values that are categorical, normally distributed, and/or not normally distributed. In some embodiments, the dataset comprises clinical data and wherein the outcome comprises a medical outcome. Thus, a predictive model can be developed and applied to other clinical data to predict outcomes more accurately.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Present invention embodiments will now be described in detail with reference to the Figures. FIG. 1 is a block diagram depicting a computing environment 100 for model development in accordance with an embodiment of the present invention. As depicted, computing environment 100 includes a client device 105, a model development server 120, and a network 155. It is to be understood that the functional division among components of computing environment 100 have been chosen for purposes of explaining present invention embodiments and is not to be construed as a limiting example.

Client device 105 includes a network interface (I/F) 106, at least one processor 107, and memory 110 that includes a client application 115. Client device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of client device 105 to send and receive data over a network, such as network 155. In general, client device 105 enables a user to perform, at model development server 120, model development operations, including feature selection, model training and testing, subpopulation analysis, and/or other tasks in accordance with present invention embodiments. Client device 105 may include internal and external hardware components, as depicted and described in further detail with respect to FIG. 7.

Client application 115 may include one or more modules or units to perform various functions of present invention embodiments described below. Client application 115 may be implemented by any combination of any quantity of software and/or hardware modules or units, and may reside within memory 110 of client device 105 for execution by a processor, such as processor 107.

Client application 115 may send instructions to model development server 120 to perform one or more operations related to data modeling. A user of client application 115 can provide one or more datasets to model development server 120 by uploading datasets or otherwise indicating locations of local and/or network-accessible datasets. Client application 115 may enable a user to submit a model development request, which can specify feature selection algorithms, machine learning algorithms, statistical techniques used to measure performance of data models, acceptable ranges of input values used to identify subpopulations, and the like. Additionally or alternatively, a user of client device 105 may, via client application 115, select trained models and apply selected models to various data processing tasks.

Model development server 120 includes a network interface (I/F) 121, at least one processor 122, and memory 125. Memory 125 may include a feature selection module 130, a propensity score matching module 135, a model training module 140, and a testing module 145. Model development server 120 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 121 enables components of model development server 120 to send and receive data over a network, such as network 155. In general, model development server 120 and its modules develop models using enhanced feature selection techniques, and apply developed models to data processing tasks in accordance with present invention embodiments. Model development server 120 may include internal and external hardware components, as depicted and described in further detail with respect to FIG. 7.

Feature selection module 130, propensity score matching module 135, model training module 140, and testing module 145 may include one or more modules or units to perform various functions of present invention embodiments described below. Feature selection module 130, propensity score matching module 135, model training module 140, and testing module 145 may be implemented by any combination of any quantity of software and/or hardware modules or units, and may reside within memory 125 of model development server 120 for execution by a processor, such as processor 122.

Feature selection module 130 analyzes datasets containing features and outcomes to identify a subset of features that are relevant to forecasting outcomes. A dataset may include a plurality of records that each include values for various features and outcomes. Each feature, also referred to as a covariate or variable or attribute, includes a value that describes a record in some manner. For example, a clinical dataset may include features of age, gender, disease status, laboratory observation, administered medication status, and the like. Additionally or alternatively, features can be extracted from clinical narrative notes using conventional or other natural language processing techniques. Thus, each record in the clinical dataset includes values for the features that together describe a patient. Additionally, each record specifies an outcome of interest (e.g., "recovered" or "not recovered"). Records that include true values (e.g., "1") for the outcome of interest are referred to as cases, and records that include false values (e.g., "0") for the outcome of interest are referred to as controls. In some embodiments, a dataset may be arranged as a tabular two-dimension data frame. For example, a set of clinical data that describes 43,000 patients in terms of 199 features may have 200 columns (one for each of the 199 features, and one indicating an outcome) and 43,000 rows (each of which includes a single patient's values for the 199 features and an outcome).

Feature selection module 130 applies one or more feature selection techniques in order to select a subset of features in a particular dataset. Feature selection module 130 may apply regression analysis in order to select features. In some embodiments, feature selection module 130 employs a least absolute shrinkage and selection operator (LASSO) algorithm to select features. The subset of features of a dataset that are selected by feature selection module 130 may be used to train a model to forecast the outcome that is indicated in the dataset.

Propensity score matching module 135 applies one or more propensity score matching techniques to a dataset to identify a subpopulation of cases and controls that are similar in terms of the values of their selected features. Thus, unlike conventional approaches in which treatment effects are adjusted relative to a set of features, present invention embodiments apply propensity score matching to match an outcome relative to features.

In particular, propensity score matching module 135 identifies case-control matchings by applying propensity score matching with different combinations of caliper values and case-control ratio values to a dataset. The propensity score matching is based on the outcome variable and on the subset of features selected by feature selection module 130. In particular, a propensity score can be calculated for features of each record with respect to the outcome, and caliper values and case-control ratio values are used to filter the results to identify matchings. The propensity score for a particular record is defined as the conditional probability of the outcome given the features. A caliper value is a numerical value that is multiplied with a standard deviation for a selected case value to define a range of acceptable control values that can be matched with the case. Equations (1) and (2) define the minimum and maximum values that a control must have to be matched to a case.

Minimum control value=(case value)−(caliper value)×(standard deviation of value for cases) (1)

Maximum control value=(case value)+(caliper value)×(standard deviation of value for cases) (2)

For example, for a feature of patient age, if a control has a value of 72 years and the standard deviation of control age values in the dataset is 10 years, then a caliper value of 0.25 indicates that the control may be matched with a case if the control has an age value of 72 years±0.25×10 years. Thus, the age of a selected control must be between 69.5 years and 74.5 years.

Propensity score matching module 135 may apply a same caliper constant to all of the feature values for a given case record in order to find a control record having corresponding feature values that are all acceptable. Thus, if no control matches a case on all feature values, then the case may be dropped from consideration.

Propensity score matching module 135 varies case-control ratio values in combination with caliper values to identify different subpopulations in a dataset. The case-control ratio value indicates the ratio of cases to controls in a given subpopulation. For example, a case-control ratio value of 1 indicates that a subpopulation has an equal number of case and control records, whereas a case-control ratio value of 2 indicates that a subpopulation has twice as many control records as case records. Propensity score matching module 135 may vary caliper values and case-control ratio values at predefined increments over a range of values to generate different combinations of caliper values and case-control ratio values. For example, a caliper value may range from 0.05 to 5.0 in increments of 0.05, and a case-control ratio value may range from 1 to 10 in increments of 1.

Propensity score matching module 135 may identify a subpopulation of cases and controls for each unique combination of caliper values and case-control ratio values. For example, a caliper value that ranges from 0.05 to 5.0 in increments of 0.05 and a case-control ratio value that range from 1 to 10 in increments of 1 results in 1,000 unique combinations of caliper values and case-control ratio values, which corresponds to 1,000 identified subpopulations of case and control records.

Each subpopulation identified by propensity score matching module 135 is processed by model training module 140 to develop a predictive model, and tested by testing module 145 to compare the similarity of cases and controls in terms of values for selected features.

Model training module 140 trains data models using whole datasets and/or portions of datasets to perform outcome forecasting. Model training module 140 may train a data model using the features selected by feature selection module 130 to forecast outcomes. Model training module 140 may train models using the selected feature values for all records of a dataset, and may train models using the selected feature values for a subpopulation of a dataset. Model training module 140 may apply conventional or other machine learning techniques to train models. In some embodiments, model training module 140 utilizes logistic regression to train a predictive model. Model training module 140 may separately train and produce a model for each subpopulation of case-control matchings identified by propensity score matching module 135.

Testing module 145 tests trained data models to determine the accuracy of models and to determine the similarity between values of cases and controls for a given trained model. In particular, testing module 145 may test a model by applying the model to a testing set of records to compare outcomes forecasted by the model to the actual outcomes. In some embodiments, testing module 145 measures a model's performance by identifying the true positives and false positives at various discrimination threshold levels. A discrimination threshold defines the threshold for a probability value to be considered a positive. For example, if a discrimination threshold is 0.5, then a probability value of 0.6 that is returned by a model is considered a positive, and a probability value of 0.4 is considered a negative. Thus, a discrimination threshold of, for example, 0.1, would be expected to return more false positives than a threshold of 0.5 for a given model.

The true positives and false positives at various discrimination thresholds are used to construct a receiver operating characteristic curve for a model. A receiver operating characteristic curve is a graphical plot of true positives against false positives at various discrimination thresholds. An area under the curve (AUC) of a receiver operating characteristic curve can then be computed by testing module 145. In general, an AUC is equal to the probability that the tested model will rank a randomly chosen positive instance higher than a randomly chosen negative one (assuming positive instances rank higher than negative instances). Inputs and/or outputs of testing module 145 may be normalized such that AUC values calculated by testing module 145 range between 0 and 1. An AUC of 0.5 may indicate that the case and control values upon which a model is trained are so similar to each other that the resulting trained model cannot discriminate cases from controls, whereas an AUC of 1.0 may indicate that the two groups can be perfectly separated by the model. Thus, a predictive model that has a higher AUC value is more accurate than a model having a lower AUC value. Moreover, when a predictive model that is trained on a subpopulation of cases and controls has an AUC of 0.5, then the subpopulation's cases and controls have similar values for each of the selected features upon which the model was trained. It should be appreciated that AUC values can be computed directly using inputs of true positive and corresponding false positives at two or more discrimination threshold levels; thus, it is unnecessary to generate a graphical plot of a receiver operating characteristic curve. Rather, any mathematical technique for approximating definite integrals can be applied to calculate AUC values. For example, trapezoidal rule approximation or Riemann sum approximation can be used to calculate AUC values.

Database 150 may include any non-volatile storage media known in the art. For example, database 150 can be implemented with a tape library, optical library, one or more independent hard disk drives, or multiple hard disk drives in a redundant array of independent disks (RAID). Similarly, data in database 150 may conform to any suitable storage architecture known in the art, such as a file, a relational database, an object-oriented database, and/or one or more tables. In some embodiments, database 150 may store data related to model development, including input datasets, training datasets, testing datasets, and resulting trained models.

Network 155 may include a local area network (LAN), a wide area network (WAN) such as the Internet, or a combination of the two, and includes wired, wireless, or fiber optic connections. In general, network 155 can be any combination of connections and protocols known in the art that will support communications between client device 105 and model development server 120 via their respective network interfaces in accordance with embodiments of the present invention.

Figure 2:
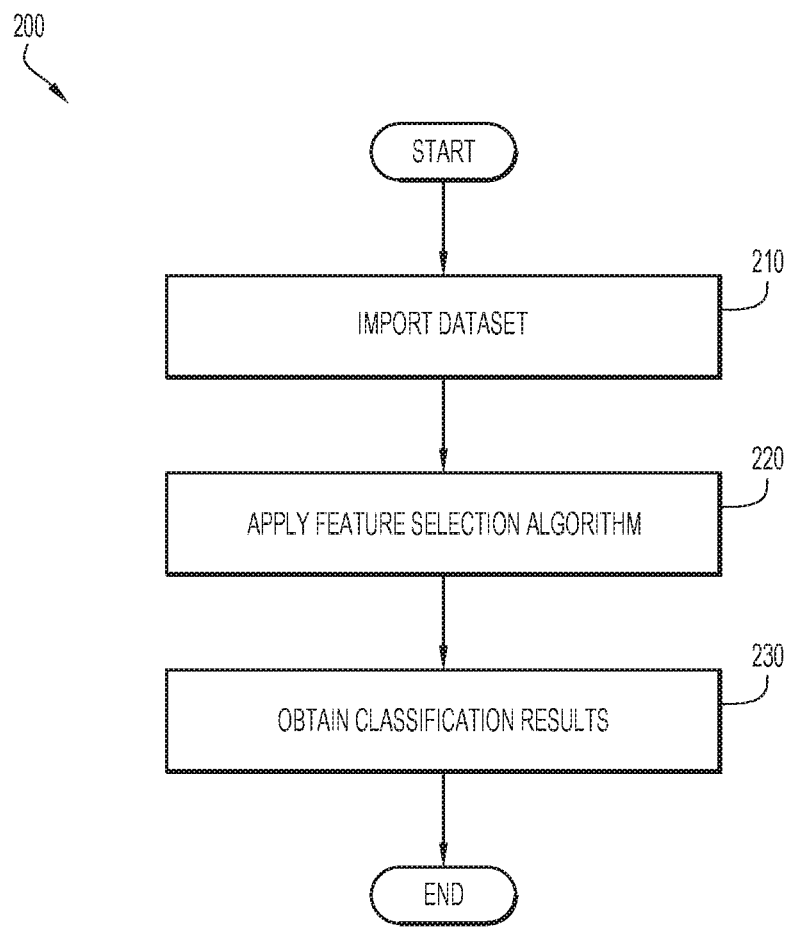
FIG. 2 is a flow chart depicting a method of selecting an initial set of features in accordance with an embodiment of the present invention.

FIG. 2 is a flow chart depicting a method 200 of selecting an initial set of features in accordance with an embodiment of the present invention.

A dataset is imported at operation 210. Feature selection module 130 may import a dataset from database 150 or client application 115 may provide feature selection module 130 with a dataset. The imported dataset may include records with values indicated for each feature (e.g., "age," "gender," "blood type," etc.), as well as an outcome of interest for a model being trained (e.g., "not recovered" or "recovered"). Cases may include any records that include true values for the outcome, and controls may include any records that include false values for the outcome.

A feature selection algorithm is applied to the dataset at operation 220. Feature selection module 130 may apply one or more conventional or other feature selection algorithms to identify a subset of features that are informative as to the outcome of a case versus a control. Feature selection module 130 may employ regression analysis in order to select a subset features. In various embodiments, feature selection module 130 may employ regression analysis techniques such as LASSO, stepwise selection, ridge regression, and the like.

Classification results are obtained at operation 230. The classification results may include an indication of the particular features of the dataset that are selected as relevant to determining outcome. For example, if a dataset has 199 features, a subset of 19 features may be identified as useful for training a model to forecast outcome.

Figure 3:
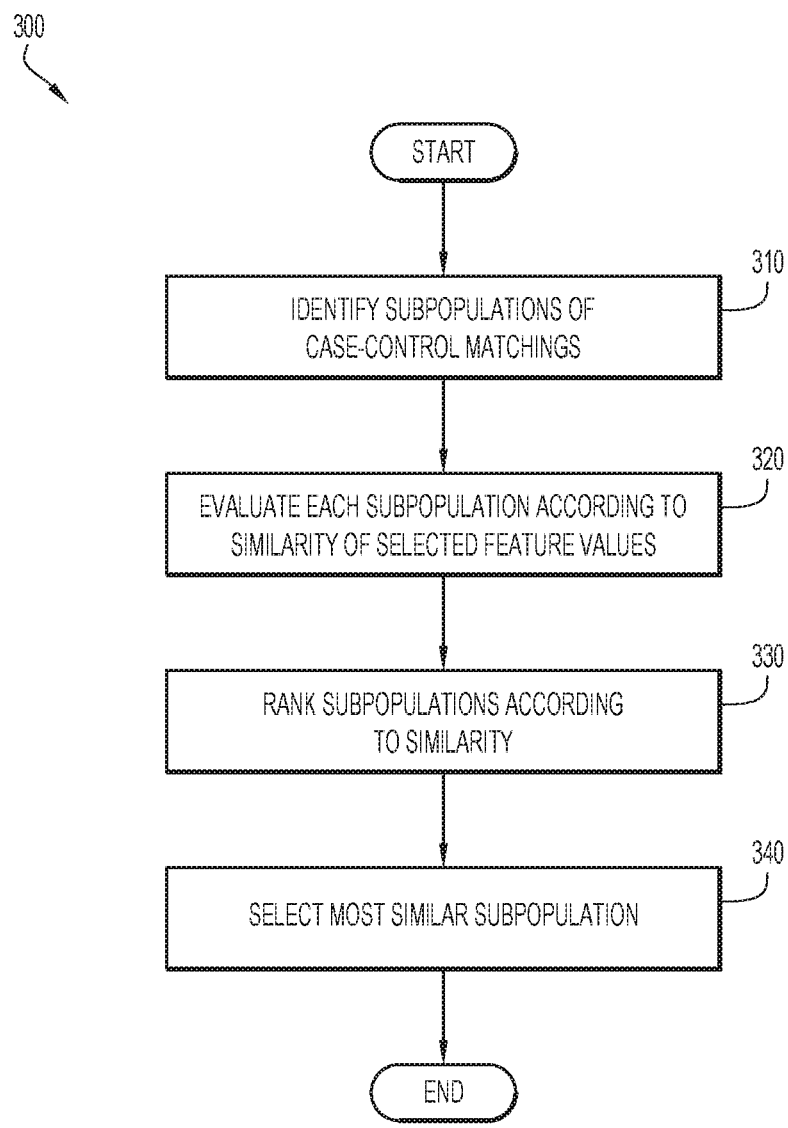
FIG. 3 is a flow chart depicting a method of identifying a subpopulation of cases and controls in accordance with an embodiment of the present invention.

FIG. 3 is a flow chart depicting a method 300 of identifying a subpopulation of cases and controls in accordance with an embodiment of the present invention.

Subpopulations of case-control matchings are identified at operation 310. Propensity score matching module 135 may use predetermined or other ranges and adjustment increments for caliper values and case-control ratio values to identify a subpopulation of case-control matchings for every possible combination of caliper value and case-control ratio value. A case is able to be matched to a control when the control's values for each selected feature (e.g., the 19 features selected in method 200) fall within the acceptable range that is defined by caliper value and standard deviation of case values, defined according to equations (1) and (2) above. A case is discarded when it cannot be matched to any control in the dataset. Cases are matched to controls until the ratio of cases to controls matches the case-control ratio value. For example, a case-control ratio value of 1 indicates a subpopulation contains an equal number of cases as controls, whereas a case-control ratio value of 3 indicates that a subpopulation contains three times as many controls as case.

Each subpopulation is evaluated according to the similarity of the selected feature values of the cases and the controls at operation 320. In particular, a subpopulation may be separated into a training set and a testing set; each case and control may randomly be assigned to either the training set or the testing set in a manner that preserves the case-control ratio in both the training set and the testing set. For example, 66% of a subpopulation's records may be assigned to a training set and 34% to a testing set, 80% of a subpopulation's records may be assigned to a training set and 20% to a testing set, and the like.

Next, model training module 140 may use the training set to train a predictive model using logistic regression considering the outcome and the selected features (e.g., the 19 features selected in method 200). The predictive model is evaluated by testing module 145 using the reserved testing set of records to identify false positives and true positives, which testing module 145 uses to compute an AUC value for the predictive model in accordance with present invention embodiments. Each subpopulation is thus processed until an AUC value is computed for all of the subpopulations.

In some embodiments, the process of dividing a subpopulation into training and testing sets, training a model, and testing the model to produce an AUC value is repeated multiple times for each subpopulation. Since the assignment of cases and controls into testing and training sets is random, multiple runs may be performed to account for variability in a subpopulation. In such embodiments, the AUC value chosen to represent a subpopulation may be an average of the AUC values of the multiple run.

The subpopulations are ranked according to similarity of the selected feature values of the cases and the controls at operation 330. Subpopulations may be ranked according to how close each subpopulation's AUC value is to 0.5; the closer a subpopulation's AUC is to 0.5, the greater the similarity between the values for the selected features of cases and controls. The most similar subpopulation is then selected at operation 340 for analysis, which is depicted and described in further detail with respect to FIG. 5.

FIG. 4 is a table 400 depicting attributes of subpopulations in accordance with an embodiment of the present invention. As depicted, each row of table 400 includes attributes of a given subpopulation, including the number of cases (column 410), the number of controls (column 420), the case-control ratio value (column 430), the caliper value (column 440), the AUC value (column 450), and the absolute value of the difference between the AUC value and 0.5 (column 460). Therefore, a smaller value in column 460 indicates a subpopulation whose cases and controls are most similar with respect to the selected feature values. In the depicted example, subpopulations have already been ranked according to AUC closeness to 0.5. Thus, among the depicted subpopulation values, the subpopulation having the most similar cases and controls (in terms of selected feature values) includes 3065 cases and a corresponding 3065 controls, which were identified among the larger input dataset according to a combination of a caliper value of 2.05 and a case-control ratio value of 1.

Figure 5:
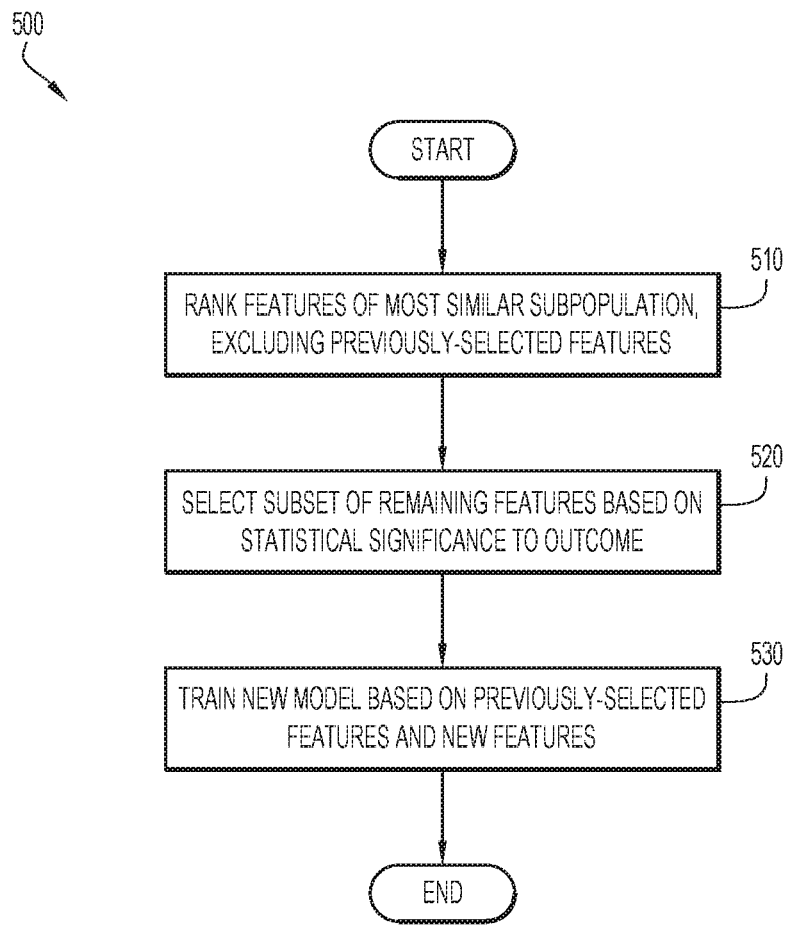
FIG. 5 is a flow chart depicting a method of applying enhanced feature selection to construct a model in accordance with an embodiment of the present invention.

FIG. 5 is a flow chart depicting a method 500 of applying enhanced feature selection to construct a model in accordance with an embodiment of the present invention.

The features of the most similar subpopulation, excluding the previously-selected features, are ranked according to their statistical significance to determining outcome at operation 510. For example, if 19 features out of 199 features in a dataset were initially selected as being outcome-relevant, the most similar subpopulation is the subpopulation having the most similar values for those 19 features, and as such, the remaining 180 unselected features of this subpopulation are analyzed to identify a subset of additional features that may be useful in distinguishing the outcome difference between the cases and controls.

A subset of the remaining features is selected based on their statistical significance to determining outcome at operation 520. In some embodiments, feature selection module 130 computes the statistical significance of each feature to the outcome in order to rank the features by significance. Feature selection module 130 may employ any conventional or other technique for quantifying the significance of a particular feature toward forecasting outcome. Statistical significance of categorical features can be calculated using a chi square test, statistical significance of normally-distributed features can be calculated using a t-test, statistical significance of continuous features that are not normally distributed can be calculated using a non-parametric test, and the like.

Once feature selection module 130 computes a statistical significance for each of the remaining features, the features can be ranked and a subset of features may be selected. In some embodiments, a predetermined number of the most statistically significant features are selected. For example, the top ten most statistically significant features may be selected, or the top 5% of features. In some embodiments, features having a statistical significance value that surpasses a predetermined threshold are selected. For example, any features having a probability value (p-value) below a threshold defined as P<0.001 may be selected.

A new model is trained using both the previously-selected features and the newly-identified features at operation 530. The new model may be trained using a same training methodology that was used to train the original model (e.g., the model trained only on the previously-selected features) so that the two models can be compared. The types of models may include any conventional or other logistical regression models.

Figure 6:
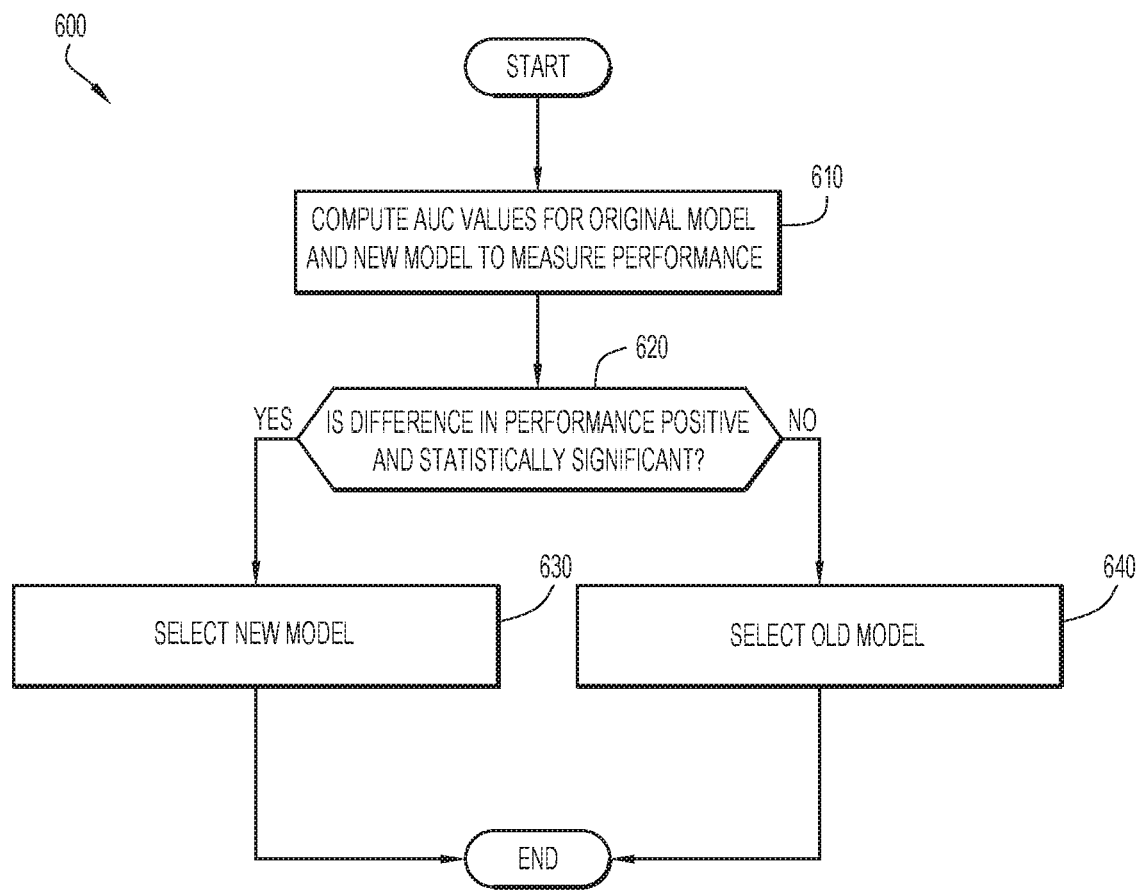
FIG. 6 is a flow chart depicting a method of evaluating model performance in accordance with an embodiment of the present invention.

FIG. 6 is a flow chart depicting a method 600 of evaluating model performance in accordance with an embodiment of the present invention.

AUC values are computed for an original model and a new model to measure their performance at operation 610. The original model, trained using the initial set of selected features, and the new model, trained similarly except using the initial set of selected features and the additional features selected by subpopulation analysis, are processed using testing module 145 to compute AUC scores. Each model may be tested using a same set of testing cases and controls. Testing module 145 obtains true and false positive rates for various discrimination thresholds, and calculates an AUC value. Testing module 145 tests each model one or multiple times; in embodiments in which models are tested multiple times, the AUC values may be averaged to compute an overall AUC value that is representative of the model.

Operation 620 determines whether the difference between the new model's performance and the original model's performance is both positive and statistically significant. The AUC value of the new model can be compared to the AUC value of the original model, and if the AUC value of the new model is closer to 1.0, then the new model's performance is considered to be superior. The difference between the AUC values may additionally be verified for statistical significance to ensure that it is practical to apply the new model instead of the original model.

If the new model's performance is superior to the original model's performance, then the new model is selected at operation 630. Otherwise, the old model is selected at operation 640. The selected model may then be applied to outcome forecasting. For example, a new dataset of records can be processed using the selected model to forecast outcomes for a particular use case. Thus, present invention embodiments enable predicting outcomes in additional databases with a higher degree of accuracy as compared to conventional techniques. Models developed according to present invention embodiments can have a variety of applications in fields such as medicine and health care, meteorology, computer science, and the like.

Figure 7:
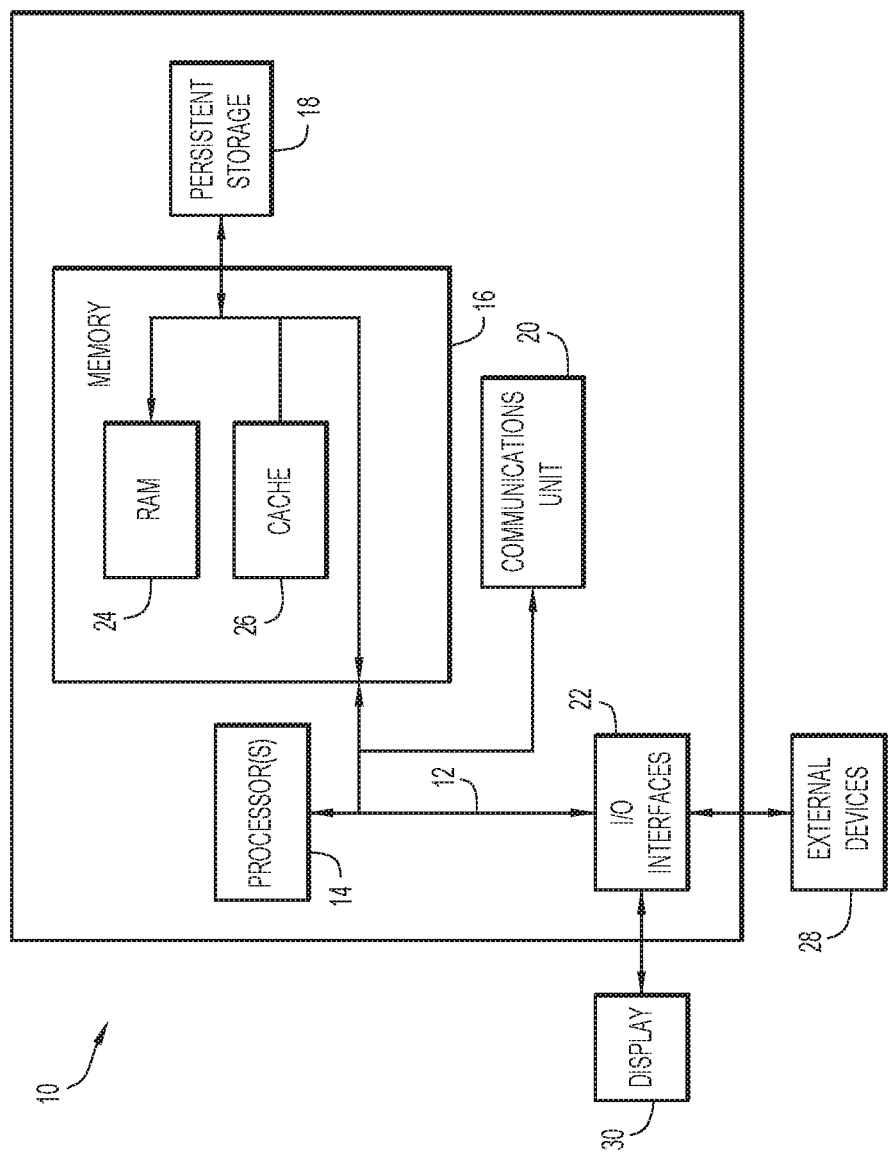
FIG. 7 is a block diagram depicting a computing device in accordance with an embodiment of the present invention.

FIG. 7 is a block diagram depicting components of a computer 10 suitable for executing the methods disclosed herein. Computer 10 may implement client device 105 and/or model development server 120 in accordance with embodiments of the present invention. It should be appreciated that FIG. 7 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to improving the performance of data models by enhancing feature selection using sub-population analysis (e.g., input datasets and corresponding metadata, trained model data, model performance data, etc.) may be stored within any conventional or other data structures (e.g., files, arrays, lists, stacks, queues, records, etc.) and may be stored in any desired storage unit (e.g., database, data or other repositories, queue, etc.). The data transmitted between client device 105 and model development server 120 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to improving the performance of data models by enhancing feature selection using sub-population analysis (e.g., input datasets and corresponding metadata, trained model data, model performance data, etc.) may include any information provided to, or generated by, client device 105 and/or model development server 120. Data relating to improving the performance of data models by enhancing feature selection using sub-population analysis may include any desired format and arrangement, and may include any quantity of any types of fields of any size to store any desired data. The data relating to improving the performance of data models by enhancing feature selection using sub-population analysis may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to improving the performance of data models by enhancing feature selection using sub-population analysis), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of improving the computerized performance of data models by enhancing feature selection using sub-population analysis.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., communications software, server software, client application 115, feature selection module 130, propensity score matching module 135, model training module 140, testing module 145, etc.). These systems may include any types of monitors and input devices (e.g., keyboard, mouse, voice recognition, etc.) to enter and/or view information.

It is to be understood that the software (e.g., communications software, server software, client application 115, feature selection module 130, propensity score matching module 135, model training module 140, testing module 145, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., communications software, server software, client application 115, feature selection module 130, propensity score matching module 135, model training module 140, testing module 145, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to improving the performance of data models by enhancing feature selection using sub-population analysis). The database system may be implemented by any number of any conventional or other databases, data stores or storage structures (e.g., files, databases, data structures, data or other repositories, etc.) to store information (e.g., data relating to improving the performance of data models by enhancing feature selection using sub-population analysis). The database system may be included within or coupled to the server and/or client systems. The database systems and/or storage structures may be remote from or local to the computer or other processing systems, and may store any desired data (e.g., data relating to improving the performance of data models by enhancing feature selection using sub-population analysis).

The present invention embodiments may employ any number of any type of user interface (e.g., Graphical User Interface (GUI), command-line, prompt, etc.) for obtaining or providing information (e.g., data relating to improving the performance of data models by enhancing feature selection using sub-population analysis), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, identifying outcome predictors in any data collected about any entities or topics.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method in a data processing system comprising at least one processor and at least one memory, the at least one memory comprising instructions executed by the at least one processor to cause the at least one processor to select features of a dataset for predictive modeling, the computer-implemented method comprising:
   selecting, from a dataset comprising a plurality of cases and controls, a first set of features that are relevant to outcome;
   identifying a subset of cases and controls having similar values for the first set of features;
   analyzing the subset of cases and controls to select a second set of additional features that are relevant to outcome;
   evaluating performance of a first predictive model against a second predictive model to determine that the second predictive model more accurately predicts outcome, wherein the first predictive model is based on the first set of features and the second predictive model is based on the first set of features and the second set of additional features; and
   utilizing the second predictive model to predict outcomes.

2. The computer-implemented method of claim 1, wherein the subset of cases and controls is identified by:
   identifying a plurality of case-control matchings by applying propensity score matching with different combinations of caliper values and case-control ratio values to the dataset to match cases with controls;
   comparing, for each case-control matching, values of the cases to values of the controls to determine a similarity value, wherein the compared values comprise values for the first set of features; and
   selecting a case-control matching based on a ranking of similarity values of the plurality of case-control matchings.

3. The computer-implemented method of claim 2, wherein the similarity value for each case-control matching is determined by:
   dividing cases and controls of the case-control matching into a training set and a testing set;
   training a predictive model using the training set;
   testing the predictive model using the testing set to identify true positives and false positives; and
   calculating the similarity value by determining an area under a receiver operating characteristic curve, wherein the receiver operating characteristic curve is based on the identified true positives and false positives.

4. The computer-implemented method of claim 1, wherein evaluating performance of the first predictive model against the second predictive model comprises:
   testing each of the first predictive model and the second predictive model using a same model testing set to identify true positives and false positives; and
   comparing a first area under a first receiver operating curve to a second area under a second receiver operating curve, wherein the first receiver operating curve is based on identified true and false positives of the first predictive model and wherein the second receiver operating curve is based on identified true and false positives of the second predictive model.

5. The computer-implemented method of claim 1, wherein the second set of additional features are identified based on a statistical significance of each feature satisfying a threshold significance value to predict the outcome.

6. The computer-implemented method of claim 5, wherein the statistical significance is determined using one or more of: a chi square test, a t-test, and a non-parametric test.

7. The computer-implemented method of claim 1, wherein the dataset comprises clinical data and wherein the outcome comprises a medical outcome.

8. A computer system for selecting features of a dataset for predictive modeling, the computer system comprising:
one or more computer processors;
one or more computer readable storage media;
program instructions stored on the one or more computer readable storage media for execution by at least one of the one or more computer processors, the program instructions comprising instructions to:
select, from a dataset comprising a plurality of cases and controls, a first set of features that are relevant to outcome;
identify a subset of cases and controls having similar values for the first set of features;
analyze the subset of cases and controls to select a second set of additional features that are relevant to outcome;
evaluate performance of a first predictive model against a second predictive model to determine that the second predictive model more accurately predicts outcome, wherein the first predictive model is based on the first set of features and the second predictive model is based on the first set of features and the second set of additional features; and
utilize the second predictive model to predict outcomes.

9. The computer system of claim 8, wherein the program instructions to identify the subset of cases and controls comprise instructions to:
identify a plurality of case-control matchings by applying propensity score matching with different combinations of caliper values and case-control ratio values to the dataset to match cases with controls;
compare, for each case-control matching, values of the cases to values of the controls to determine a similarity value, wherein the compared values comprise values for the first set of features; and
select a case-control matching based on a ranking of similarity values of the plurality of case-control matchings.

10. The computer system of claim 9, wherein the similarity value for each case-control matching is determined by:
dividing cases and controls of the case-control matching into a training set and a testing set;
training a predictive model using the training set;
testing the predictive model using the testing set to identify true positives and false positives; and
calculating the similarity value by determining an area under a receiver operating characteristic curve, wherein the receiver operating characteristic curve is based on the identified true positives and false positives.

11. The computer system of claim 8, wherein the program instructions to evaluate performance of the first predictive model against the second predictive model comprise instructions to:
test each of the first predictive model and the second predictive model using a same model testing set to identify true positives and false positives; and
compare a first area under a first receiver operating curve to a second area under a second receiver operating curve, wherein the first receiver operating curve is based on identified true and false positives of the first predictive model and wherein the second receiver operating curve is based on identified true and false positives of the second predictive model.

12. The computer system of claim 8, wherein the second set of additional features are identified based on a statistical significance of each feature satisfying a threshold significance value to predict the outcome.

13. The computer system of claim 12, wherein the statistical significance is determined using one or more of: a chi square test, a t-test, and a non-parametric test.

14. The computer system of claim 8, wherein the dataset comprises clinical data and wherein the outcome comprises a medical outcome.

15. A computer program product for selecting features of a dataset for predictive modeling, the computer program product comprising one or more computer readable storage media collectively having program instructions embodied therewith, the program instructions executable by a computer to cause the computer to:
select, from a dataset comprising a plurality of cases and controls, a first set of features that are relevant to outcome;
identify a subset of cases and controls having similar values for the first set of features;
analyze the subset of cases and controls to select a second set of additional features that are relevant to outcome;
evaluate performance of a first predictive model against a second predictive model to determine that the second predictive model more accurately predicts outcome, wherein the first predictive model is based on the first set of features and the second predictive model is based on the first set of features and the second set of additional features; and
utilize the second predictive model to predict outcomes.

16. The computer program product of claim 15, wherein the program instructions to identify the subset of cases and controls cause the computer to:
identify a plurality of case-control matchings by applying propensity score matching with different combinations of caliper values and case-control ratio values to the dataset to match cases with controls;
compare, for each case-control matching, values of the cases to values of the controls to determine a similarity value, wherein the compared values comprise values for the first set of features; and
selecting a case-control matching based on a ranking of similarity values of the plurality of case-control matchings.

17. The computer program product of claim 16, wherein the similarity value for each case-control matching is determined by:
dividing cases and controls of the case-control matching into a training set and a testing set;
training a predictive model using the training set;
testing the predictive model using the testing set to identify true positives and false positives; and
calculating the similarity value by determining an area under a receiver operating characteristic curve, wherein the receiver operating characteristic curve is based on the identified true positives and false positives.

18. The computer program product of claim 15, wherein the program instructions to evaluate performance of the first predictive model against the second predictive model cause the computer to:

test each of the first predictive model and the second predictive model using a same model testing set to identify true positives and false positives; and compare a first area under a first receiver operating curve to a second area under a second receiver operating curve, wherein the first receiver operating curve is based on identified true and false positives of the first predictive model and wherein the second receiver operating curve is based on identified true and false positives of the second predictive model.

19. The computer program product of claim 15, wherein the second set of additional features are identified based on a statistical significance of each feature satisfying a threshold significance value to predict the outcome.

20. The computer program product of claim 19, wherein the statistical significance is determined using one or more of: a chi square test, a t-test, and a non-parametric test.

* * * * *